(12) United States Patent
Kim et al.

(10) Patent No.: US 12,203,132 B2
(45) Date of Patent: Jan. 21, 2025

(54) METHOD FOR DETERMINING FETAL FRACTION IN MATERNAL SAMPLE

(71) Applicant: THERAGEN GENOMECARE CO., LTD., Suwon-si (KR)

(72) Inventors: Sun Shin Kim, Gyeonggi-do (KR); Min Jeong Kim, Incheon (KR)

(73) Assignee: THERAGEN GENOMECARE CO., LTD., Geyonggi-Do (KR)

( * ) Notice: Subject to any disclaimer, the term of this patent is extended or adjusted under 35 U.S.C. 154(b) by 712 days.

(21) Appl. No.: 16/956,477

(22) PCT Filed: Feb. 5, 2018

(86) PCT No.: PCT/KR2018/001497
§ 371 (c)(1),
(2) Date: Jun. 19, 2020

(87) PCT Pub. No.: WO2019/124629
PCT Pub. Date: Jun. 27, 2019

(65) Prior Publication Data
US 2020/0347442 A1 Nov. 5, 2020

(30) Foreign Application Priority Data

Dec. 22, 2017 (KR) .......................... 10-2017-0178473

(51) Int. Cl.
*C12Q 1/6827* (2018.01)
*G16B 20/20* (2019.01)

(52) U.S. Cl.
CPC .......... *C12Q 1/6827* (2013.01); *G16B 20/20* (2019.02); *C12Q 2600/166* (2013.01)

(58) Field of Classification Search
CPC ............ C12Q 1/6827; C12Q 2600/166; C12Q 2600/156; C12Q 1/6881; C12Q 1/6888; C12Q 2600/158; G16B 20/20; G16B 20/00; G16B 30/00
See application file for complete search history.

(56) References Cited

U.S. PATENT DOCUMENTS

| | | | |
|---|---|---|---|
| 2005/0009069 A1* | 1/2005 | Liu ...................... | C12Q 1/6827 702/20 |
| 2012/0165203 A1 | 6/2012 | Quake et al. | |
| 2012/0196754 A1 | 8/2012 | Quake et al. | |
| 2015/0232937 A1* | 8/2015 | Oliphant .............. | C12Q 1/6881 506/9 |

FOREIGN PATENT DOCUMENTS

| KR | 10-2016-0013183 A | 2/2016 |
|---|---|---|
| KR | 10-2017-0140107 A | 12/2017 |

OTHER PUBLICATIONS

Fan et al., Nature, 487 (7407): 320-324, July (Year: 2012).*
Roshyara, BMC Genetics, 15(88): 1-11 (Year: 2014).*
Kim et al., Bioinformatics, 34(7), 1086-1091, (Nov. 8, 2017).*
Swanson et al., Current Genet. Med. Rep., 1: 113-121, (Year: 2013).*
Xu et al., A Method to Quantify Cell-Free Fetal DNA Fraction in Maternal Plasma Using Next Generation Sequencing: Its Application in Non-Invasive Prenatal Chromosomal Aneuploidy Detection, PLOS ONE, DOI: 10.1371/journal.pone.0146997, Jan. 14, 2016, 13 pages.
Kim et al., Cost-effective and accurate method of measuring fetal fraction using SNP imputation, Bioinformatics, Oxford University Press, Nov. 8, 2017, 6 pages.
Jiang et al., FetalQuantSD; accurate quantification of fetal DNA fraction by shallow-depth sequencing of maternal plasma DNA., Center of Excellence in Genomic Medicine Research/Macmilian Publishers Limited, May 11, 2016, 7 pages.
Liu et al., Systematic assessment of imputation performance using the 1000 Genomes reference panels, Briefings in Bioinformatics vol. 16. No. 4, 549-562, Sep. 22, 2014, 14 pages.
Peng et al., Bioinformatics Approaches for Fetal DNA Fraction Estimation in Noninvasive Prenatal Testing, International Journal of Molecular Sciences, 18, 453; DOI: 10.3390/ijms18020453, Feb. 20, 2017, 9 pages.
International Search Report and Written Opinion for related International Application No. PCT/KR2018/001497, mailed on Sep. 21, 2018; 9 pages.
Office Action for related Korean Application No. 10-2017-0178473, mailed on May 21, 2019, 5 pages.
Notice of Allowance for related Korean Application No. 10-2017-0178473, mailed on Sep. 9, 2019, 2 pages.
Norton et al., "Cell-free DNA Analysis for Noninvasive Examination of Trisomy", The New England Journal of Medicine, 2015, 9 pages.
Kim et al., "Prospective observations study protocol to investigate cost-effectiveness of various prenatal test strategies after the introduction of noninvasive prenatal testing", BMC Pregnancy and Childbirth (2018) 18:307. https://doi.org/10.1186/s12884-018-1930-y, 7 pages.
Zhytnik et al., "Reproductive options for families at risk of Osteogenesis Imperfecta: a review", Orphanet Journal of Rare Diseases (2020) 15:128, https://doi.org/10.1186/s13023-020-01404-w, 20 pages.

* cited by examiner

*Primary Examiner* — Cynthia B Wilder
(74) *Attorney, Agent, or Firm* — Procopio, Cory, Hargreaves & Savitch LLP (57) ABSTRACT

Provided are a method for determining a fetal fraction and a computer readable medium in which a program to be applied to performing the method is recorded. According to the method, the fetal fraction may be accurately determined even for a small sequencing coverage. Therefore, highly cost-efficient and accurate measurement of a fetal fraction may be performed.

12 Claims, 5 Drawing Sheets

A. BEFORE IMPUTATION

B. IMPUTATION WITH HRC v1.1

C. IMPUTATION WITH 1000GP3

FIG. 4

METHOD FOR DETERMINING FETAL FRACTION IN MATERNAL SAMPLE

TECHNICAL FIELD

The present disclosure relates to a method of determining a fetal fraction in a biological sample derived from a pregnant woman and software related to the method.

BACKGROUND ART

Prenatal diagnosis refers to diagnosis of the presence or absence of diseases in a fetus before the fetus is born. Prenatal diagnosis is largely classified into an invasive diagnostic test and a non-invasive diagnostic test (NIPT). Invasive diagnostic tests include, for example, chorionic villus sampling, amniocentesis, and umbilical cord. Invasive diagnostic tests may cause abortion or diseases by impacting a fetus during the examination process, and therefore, non-invasive diagnostic tests have been developed.

Recently, it has been demonstrated that non-invasive diagnosis of fetal chromosomal aneuploidy is feasible by massively parallel sequencing of DNA molecules in the plasma of pregnant women. Fetal DNA is detectable in maternal plasma and serum from the seventh week of gestation, and the amount of fetal DNA in maternal blood increases as pregnancy progresses. The ratio of fetal DNA among cell-free DNA (cfDNA) isolated from maternal blood is referred to as a fraction of fetal nucleic acids or a fetal fraction. The smaller the fetal fraction, the higher the diagnostic error of chromosome aneuploidy, and thus the fetal fraction may affect the accuracy of the non-invasive prenatal diagnosis test.

Regarding a method of measuring the fetal fraction, a single nucleotide polymorphism (SNP)-based method has high accuracy, but there is a problem in that a cost of the genotyping is high (Jiang P. et al., Bioinformatics, 2012, vol. 28, pp. 2883-2890), and a Y chromosome-based method is simple but has a problem in that it only applies to male fetuses (Hudecova I. et al., PloS one, 2014, vol. 9, p.e88484). Also, machine learning had an advantage of no additional costs but has a problem of less accuracy (Johansen P. et al., Prenatal diagnosis, 2016, vol. 36, pp. 530-536).

Therefore, for accurate prenatal diagnosis tests, a method of measuring a fetal fraction with excellent accuracy needs to be developed.

DESCRIPTION OF EMBODIMENTS

Technical Problem

Provided is a method of determining a fetal fraction.

Provided is a computer readable medium, in which a program to be applied to performing the method of determining a fetal fraction is recorded.

Solution to Problem

According to an aspect of the present disclosure, provided is a method of determining a fetal fraction, wherein the method includes
obtaining sequence information (reads) of a plurality of nucleic acid fragments from a biological sample of a pregnant woman;
genotyping single nucleotide polymorphisms (SNPs) from the biological sample;
measuring single nucleotide variants (SNVs) by performing an SNP imputation on the genotyped SNPs;
measuring a non-maternal allele fraction based on the obtained reads and the SNVs; and
determining a fetal fraction from the non-maternal allele fraction.

As used herein, the term "fetal fraction" or "fraction of fetal nucleic acids" refers to an amount of fetal nucleic acids among nucleic acids isolated from a biological sample of a pregnant woman. The fetal fraction may be a concentration, a relative ratio, or an absolute amount of the fetal nucleic acids. The fetal nucleic acids may be a nucleic acid derived from a fetal placenta trophoblast.

The method includes obtaining reads of a plurality of nucleic acid fragments from a biological sample of a pregnant woman.

The biological sample may be blood, plasma, serum, urine, saliva, mucus, sputum, feces, tears, or a combination thereof. The biological sample may be, for example, plasma of the peripheral blood. The biological sample may contain nucleic acids derived from mother of fetus. The nucleic acids may be cell-free DNA (cfDNA). The nucleic acids may be isolated DNA.

The obtaining of the reads may include isolating cfDNA from the biological sample. The isolating of nucleic acids from the biological sample may be performed by a method known to those skilled in the art. The isolated nucleic acid fragments may be about 10 bp (base pairs) to about 2000 bp, about 15 bp to about 1500 bp, about 20 bp to about 1000 bp, about 20 bp to about 500 bp, about 20 bp to about 200 bp, or about 20 bp to about 100 bp in length.

The obtaining of the sequence information of a plurality of nucleic acid fragments from the biological sample of a pregnant woman may include performing massively parallel sequencing of the obtained nucleic acids. The term "massively parallel sequencing" may be used interchangeably with next-generation sequencing (NGS) or second-generation sequencing. The massively parallel sequencing refers to a technique in which millions of nucleic acid fragments are sequenced simultaneously. The massively parallel sequencing may be performed in parallel by, for example, 454 platform (Roche), GS FLX titanium, Illumina MiSeq, Illumina HiSeq, Illumina Genome Analyzer, Solexa platform, SOLiD System (Applied Biosystems), Ion Proton (Life Technologies), Complete Genomics, Helicos Biosciences Heliscope, single molecule real-time sequencing technology (SMRT™) of Pacific Biosciences, or a combination thereof.

The obtained sequence information of the nucleic acid fragments may be also called reads.

The term "sequencing coverage" is also referred to as a sequencing depth, which denotes a number of reads that include a given nucleotide in the sequence reconstructed by massive parallel sequencing. In order to distinguish between sequencing errors and actual nucleotide polymorphism, an accuracy of sequencing needs to be increased by sequencing individual genomes several times. The sequencing coverage may be an average number of sequence information that is subjected to be sequenced. The sequencing coverage may be calculated from Equation of (length of reads×number of reads)/haploid genome length. The sequencing coverage of the obtained sequence information may be about 0.00001 to about 1, about 0.0001 to about 0.5, about 0.001 to about 0.1, about 0.001 to about 0.05, about 0.003 to about 0.05, about 0.005 to about 0.05, about 0.007 to about 0.04, about 0.01 to about 0.03, about 0.015 to about 0.03, about 0.02 to about 0.03, about 0.025 to about 0.03, about 0.01 to about 0.025, about 0.01 to about 0.02, or about 0.01 to about 0.015.

The method includes genotyping SNPs from the biological sample. The biological sample used to genotype SNPs may be a maternal buffy coat. The term "single nucleotide polymorphism (SNP)" refers to a genetic change or variation that shows a single nucleotide sequence (A, T, G, or C) difference in the genome. The SNP may occur at a position where at least two allele sequences present at a frequency of 1% or more in a human population. A genotyping of the SNPs may be performed by a method known in the art of biotechnology. For example, the genotyping of the SNPs may be performed by SNP microarray.

When the SNPs are genotyped from the obtained biological sample, the SNPs or a ratio of the SMP alleles may be analyzed. A number of the genotyped SNPs may be about 10 to about 10,000,000, about 100 to about 5,000,000, about 100 to about 3,000,000, about 1,000 to about 1,000,000, about 1,000 to about 700,000, about 1,000 to about 500,000, about 1,000 to about 300,000, about 1,000 to about 100,000, or about 10,000 to about 100,000.

The method includes measuring single nucleotide variants (SNVs) by performing an SNP imputation on the SNPs.

The SNP imputation may include determining missing SNPs by comparing the genotyped SNPs with a reference panel. The SNP imputation refers statistically estimating unobserved genotypes. A data of genotypes may be constructed from a large amount of sequence information, and thus unobserved genotypes in the actual sample may be estimated by using the constructed genotype information as a reference panel. The reference panel may be selected from the group consisting of HapMap, Haplotype Reference Consortium (HRC) v1.1, 1000Genome phase 1 (1000GP1), 1000Genome phase 3 (1000GP3), and Consortium on Asthma among African-ancestry Populations in the Americas (CAAPA).

The SNP imputation may be performed by using a software selected from the group consisting of MaCH, Minimac, IMPUTE2, Beagle, and SHAPEIT2. By performing the SNP imputation, a number of SNPs subjected to be genotyped may be amplified by adding the estimated SNPs to the SNPs found in the actual sample.

The method may further include filtering a minor allele frequency (MAF) after measuring the SNVs. The filtering of the MAF may exclude SNVs having a MAF value less than a standard or a threshold. The filtering of the MAF may be performed on SNVs of at least one selected from chromosome 1 to chromosome 22, X chromosome, and Y chromosome in case of a human. The filtering of the MAF may be performed on at least one chromosome, for example, all chromosomes. The filtering of the MAF may be performed on chromosome 3 or chromosome 4. The filtering of the MAF may include excluding SNVs having an MAF value less than about 0.5% with respect to chromosome 4, excluding SNVs having an MAF value less than about 7% with respect to chromosome 3, or a combination thereof. When the SNP imputation is performed using a reference panel, HRC v1.1, the SNVs having a MAF value less than about 0.5% with respect to chromosome 4 may be excluded. When the SNP imputation is performed using a reference panel, 1000GP3, the SNVs having a MAF value less than about 7% with respect to chromosome 3 may be excluded.

The method may include measuring a non-maternal allele fraction based on the obtained reads and the SNVs. The non-maternal allele fraction may calculate based on a number of the obtained reads and a number of alleles in a maternal homozygous site.

The method includes determining a fetal fraction from the non-maternal allele fraction. The non-maternal allele fraction (%) may be measured from the result of the genotyping of the SNPs and the reads mapped in a reference genome. For example, a locus corresponding to the maternal homozygous genotype in the result of the genotyping of the SNPs may be selected, and a number of maternal alleles and a number of non-maternal alleles in the sequence information mapped at the loci may be used to measure the non-maternal allele fraction (%).

The fetal fraction may be measured by a regression equation between the non-maternal allele fraction (%) and a fetal DNA fraction (%). For example, the fetal fraction may be determined as defined in Equation 1 or Equation 2:

$$F=10.54X-15.42 \quad \text{(Equation 1); and}$$

$$F=5.76X-17.36 \quad \text{(Equation 2).}$$

In Equation 1 and Equation 2, F is a fetal fraction (%), X is a non-maternal allele fraction (%).

When the SNP imputation is performed using a HRC v1.1 reference panel, a fetal fraction may be calculated according to Equation 1, F=10.54X−15.42. When the SNP imputation is performed using a 1000GP3 reference panel, a fetal fraction may be calculated according to Equation 2, F=5.76X−17.36.

According to another aspect of the present disclosure, provided is a computer readable medium in which a program to be applied to performing the method is recorded. The computer readable medium includes a system including a computer readable medium.

Advantageous Effects of Disclosure

According to one or more embodiments, when a method of determining a fetal fraction and a computer readable medium in which a program to be applied to performing the method is recorded are used, a fetal fraction may be accurately determined even for a small sequencing coverage. Therefore, highly cost-efficient and accurate measurement of a fetal fraction may be performed.

MODE OF DISCLOSURE

Hereinafter, the present invention will be described in more detail with reference to Examples. However, these examples are for illustrative purposes only and the scope of the present invention is not limited to these examples.

Example 1. Measurement of Fetal Fraction

1. Sample Preparation and Determination of Baseline Fetal Fraction

A total of 84 pregnant women (42 male and 42 female fetuses) were enrolled at hospitals. Blood was drawn from each of the enrolled pregnant women, and serum and maternal buffy coat were obtained from the blood. A semiconductor sequencing analysis was performed on the obtained serum. To measure fetal fractions using SNPs, the maternal buffy coat was genotyped using the Affymetrix 6.0 (about 900K SNPs).

An average of 247,596 (about 250K) SNP genotypes in 84 samples (mean 5,351,786 reads, 0.3× sequencing coverage) and a linear regression model (Y=18.9X−6.6) were used to calculated the fetal fractions. The linear regression model used herein was a method disclosed in Jiang. P. et al., (2016) FetalQuant$^{SD}$: accurate quantification of fetal DNA fraction by shallow-depth sequencing of maternal plasma DNA, npj Genomic Medicine, 1, 16013. The calculated fetal fractions were used as baseline fetal fractions.

2. Performing SNP Imputation

Two factors affecting the accuracy of an SNP-based method are read depth (coverage) during sequencing and the number of SNPs. A higher coverage and larger number of SNPs leads to more accurate comparison of maternal and fetal DNA fragments, but maintaining high coverage is costly and time-consuming. By lowering the coverage, the cost of the sequencing step can be reduced. However, the accuracy of fetal fraction measurement decreases as coverage decreases.

In this regard, first, the number of SNPs was increased by performing an SNP imputation to maintain the accuracy of fetal fraction measurement while lowering the coverage. In the SNP imputation, a larger number of SNPs were estimated through comparison with a reference panel based on mass DNA information related to genetic variations. A 1000Genome phase 3 (1000GP3) panel and a HRC v1.1 panel were used as reference panels. The 1000GP3 panel is a reference panel based on genetic information obtained from 2,504 humans (Genomes Project C. et al. (2015) A global reference for human genetic variation, Nature, 526, 68-74), and the HRC v1.1 panel is a reference panel that is recently developed by using 32 470 samples (McCarthy S. et al., (2016) A reference panel of 64,976 haplotypes for genotype imputation, Nature genetics, 48, 1279-1283). Although HRC v1.1 showed the highest accuracy among all reference panels ($R^2$=0.98), it requires the most time because of the large amount of information it contains. While 1000GP3 showed lower accuracy than HRC v1.1 ($R^2$=0.96), it requires less time and computing power. Thus, both the HRC v1.1 panel and the 1000GP3 panel were used for SNP imputation.

However, because the HRC v1.1 reference panel was very large, the Michigan Imputation Server was used. In addition, minimac3, which showed the highest performance among all imputation service tools, was used. SHAPEIT2 was used in the phasing step.

The average numbers of SNPs in the 84 samples before and after performing the SNP imputation are shown in Table 1.

TABLE 1

| | Before SNP imputation | After SNP imputation | |
|---|---|---|---|
| Reference panel | — | HRC v1.1 | 1000GP3 |
| Average number of SNPs | 247,596 | 10,254,299 | 11,319,299 |

3. Filtering According to Minor Allele Frequency (MAF)

When analyzing imputed SNVs, it is important to estimate MAFs. In general, an MAF>5% indicates common variants, 0.5%≤MAF<5% indicate low-frequency variants, and an MAF<0.5% indicates rare variants. Estimated SNVs at extremely low MAFs are not reliable.

As described in Example 1.2, the number of SNPs increased through the SNP imputation, but the accuracy of imputation decreased since the MAFs decreased in the entire reads. In order to select SNVs having high accuracy from the results of performing the imputation, SNVs were removed from the reads by performing MAF filtering.

Because the calculation of fetal fractions across the entire genome requires a substantial amount of time, only specific chromosomes were analyzed in the experiment. To determine which chromosomes are be used in the MAF filtering test, a fraction of non-maternal alleles of each chromosome of the 84 samples were measured using SNVs imputed using HRC v1.1 or 1000GP3. Particularly, in the results of the SNP genotype analysis, a locus corresponding to a maternal homozygous genotype (AA genotype) was identified, and a number of the non-maternal alleles (B) was divided by the sum of a number of the maternal alleles (A) and the number of the non-maternal alleles (A+B) from the sequence information mapped at the locus to calculate a fraction (B×100/(A+B)) (%).

Figure 1A:
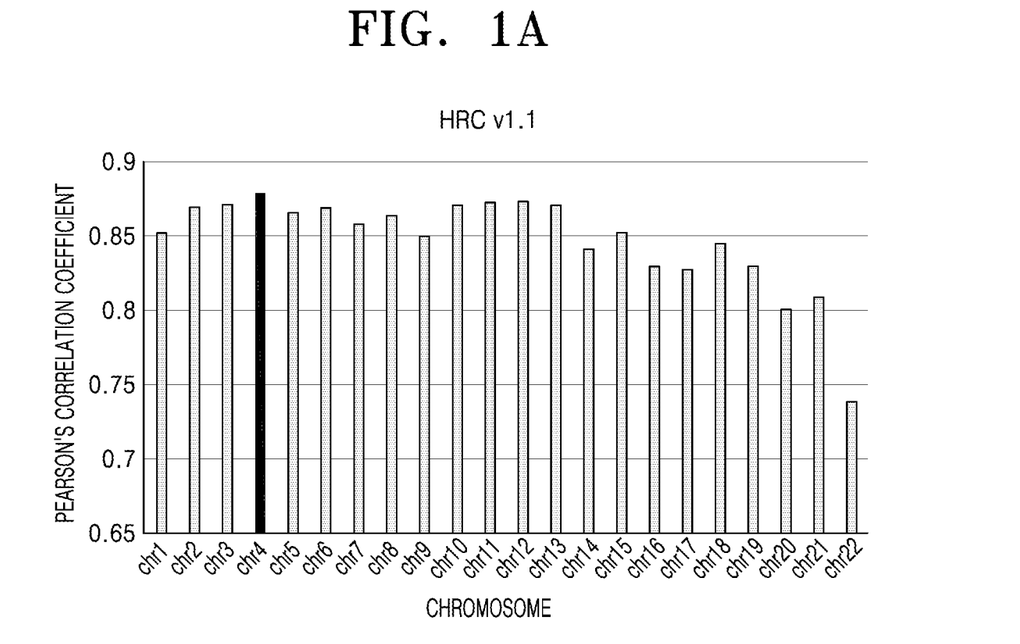
FIGS. 1A and 1B are respectively graphs showing the Pearson's correlation between a baseline and a non-maternal allele fraction measured in each of chromosomes by using SNVs imputed with a HRC v1.1 panel and a 1000GP3 panel.
Figure 1B:
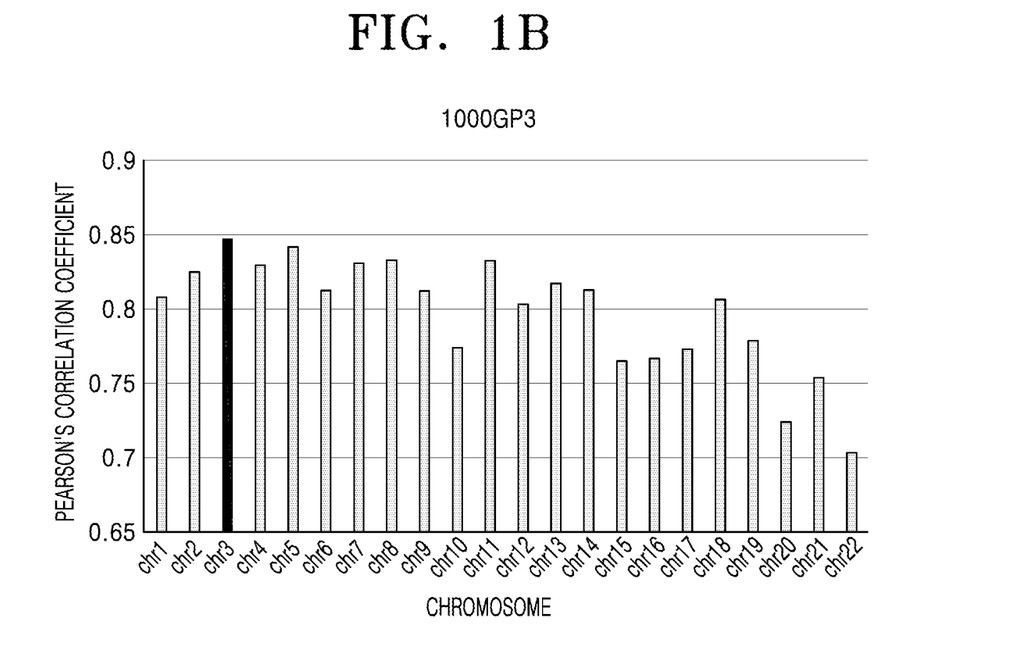

Pearson's correlations between the measured fractions of non-maternal alleles of each chromosome and baseline were obtained, and the results are shown in FIGS. 1A and 1B. (FIG. 1A: SNVs imputed using HRC v1.1 panel were used, FIG. 1B: SNVs imputed using 1000GP3 panel were used).

As shown in FIGS. 1A and 1B, when the HRC v1.1 was used, chromosomes 4 and 12 showed strong correlations, with correlation coefficients (r) of 0.88 and 0.87, respectively. When 1000GP3 was used, chromosomes 3 and 5 showed strong correlations, with correlation coefficients (r) of 0.85 and 0.84. MAF filtering was performed using chromosome 4 (HRC v1.1) and chromosome 3 (1000GP3), which showed the highest correlation coefficients.

In order to perform the MAF filtering, a MAF standard (0.05%, 0.1%, 0.5%, 1.0%, 5.0%, or 7.0%) was set, and all SNVs with MAF values less than this standard were removed. After filtering according to the MAF standard, the Pearson's correlation coefficients between the fractions of non-maternal alleles and baseline were calculated. The correlation coefficients with the fetal fractions measured by using a Y chromosome-based method (Hudecova I. et al., (2014) Maternal plasma fetal DNA fractions in pregnancies with low and high risks for fetal chromosomal aneuploidies, PloS one, 9, e88484) were calculated for comparison. The chromosome, MAF standard, number of SNVs, and correlation coefficient are shown in Table 2.

TABLE 2

| Chromosome No. | MAF (%) | Number of SNVs | Correlation coefficient (with baseline results) | Correlation coefficient (with Y chromosome-based results) |
|---|---|---|---|---|
| Using HRC v1.1 reference panel | | | | |
| Chr 1-22 | No filtering | 10,254,299 | 0.895541 | 0.818936 |
|  | 0.5 | 2,178,642 | 0.989103 | 0.940416 |
| Chr 4 | 0.05 | 239,480 | 0.959516 | 0.895125 |
|  | 0.1 | 207,879 | 0.961378 | 0.899338 |
|  | 0.5 | 153,542 | 0.965898 | 0.913379 |
|  | 1.0 | 131,873 | 0.965004 | 0.920041 |
|  | 5.0 | 94,059 | 0.964265 | 0.929434 |
|  | 7.0 | 85,837 | 0.961283 | 0.929671 |
| Using 1000GP3 reference panel | | | | |
| Chr 1-22 | No filtering | 11,319,299 | 0.895541 | 0.818936 |
|  | 7.0 | 1,438,097 | 0.984177 | 0.938047 |
| Chr 3 | 0.05 | 379,656 | 0.922658 | 0.859184 |
|  | 0.1 | 305,392 | 0.932695 | 0.877276 |
|  | 0.5 | 191,068 | 0.951134 | 0.899850 |
|  | 1.0 | 158,786 | 0.955757 | 0.907368 |
|  | 5.0 | 111,891 | 0.961318 | 0.924088 |
|  | 7.0 | 101,429 | 0.962534 | 0.925300 |

Figure 2A:
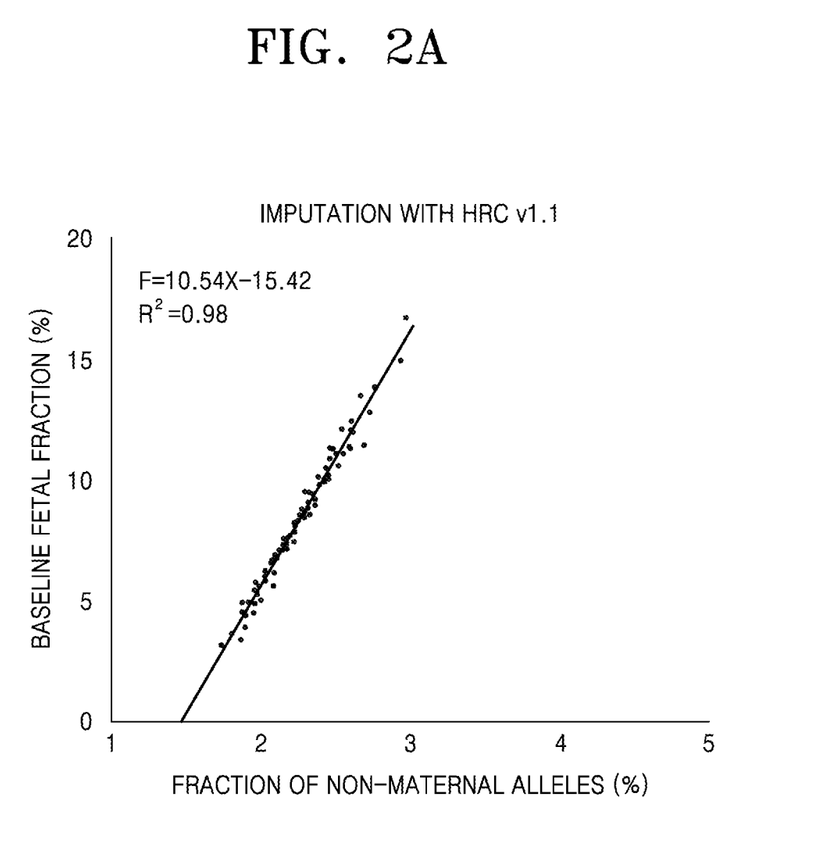
FIGS. 2A and 2B are respectively graphs showing the correlation between a baseline fetal fraction and an estimated non-maternal allele fraction after performing an imputation using a HRC v1.1 panel and a 1000GP3 panel.
Figure 2B:
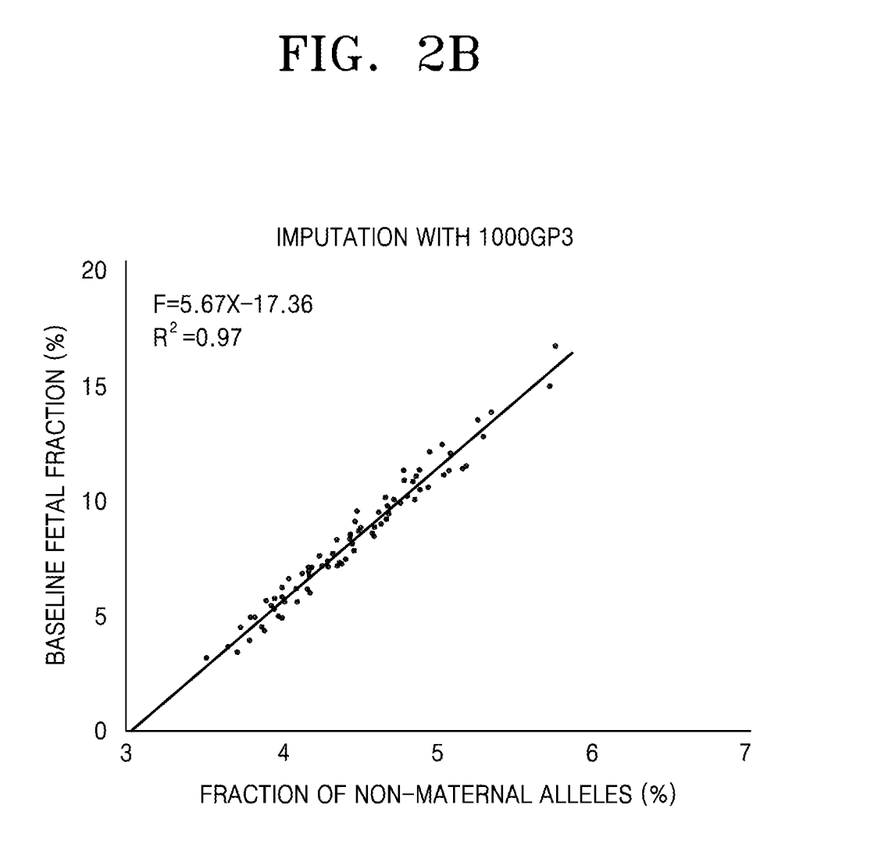

As shown in Table 2, for HRC v1.1, the correlation coefficient with the baseline was highest when SNVs with MAF values less than 0.5% were removed (r=0.97 in chromosome 4, r=0.99 in chromosomes 1 to 22). For 1000GP3, the correlation coefficient was highest when SNVs with MAF values less than 7% were removed (r=0.96 in chromosome 3, r=0.98 in chromosomes 1 to 22). The graphs showing the correlation between the estimated non-maternal allele fractions after imputation and the baseline fetal fractions are shown in FIGS. 2A and 2B, and the following regression Equations were derived (F: fetal fraction, X: non-maternal allele fraction).

Regression Equation regarding HRC v1.1:
$$F = 10.54X - 15.42 \quad \text{(Equation 1)}$$

Regression Equation regarding 1000GP3: 
$$F = 5.76X - 17.36 \quad \text{(Equation 2)}$$

In cases of using HRC v1.1 and applying a threshold of MAF 0.5% in chromosomes 1 to 22, estimated non-maternal allele fractions after imputation (X), fetal fractions calculated from Equation 1 (F), and baseline fetal fractions are shown in Table 3. In cases of using 1000GP3 and applying a threshold of MAF 7% in chromosomes 1 to 22, estimated non-maternal allele fractions after imputation (X), fetal fractions calculated from Equation 2 (F), and baseline fetal fractions are shown in Table 4.

TABLE 4

| Non-maternal allele fraction | Estimated fetal fraction (HRC v1.1) | Baseline fetal fraction | Non-maternal allele fraction | Estimated fetal fraction (HRC v1.1) | Baseline fetal fraction |
|---|---|---|---|---|---|
| 1.964956644 | 5.290643031 | 5.761554111 | 1.804410796 | 3.598489795 | 3.636890661 |
| 2.461304338 | 10.52214772 | 10.11203623 | 2.193336116 | 7.697762662 | 7.742588045 |
| 2.731353683 | 13.36846782 | 12.85038896 | 2.25176226 | 8.313574218 | 8.395942656 |
| 2.428680649 | 10.17829404 | 9.959589059 | 1.961055571 | 5.249525716 | 5.47941978 |
| 2.543951197 | 11.39324562 | 12.16462095 | 2.386417888 | 9.732844535 | 10.18235405 |
| 2.414464277 | 10.02845348 | 10.09884697 | 2.359290507 | 9.446921944 | 9.01684116 |
| 1.890512794 | 4.506004846 | 3.945468953 | 2.50660571 | 10.99962418 | 11.13212246 |
| 2.436519704 | 10.26091768 | 10.54402542 | 2.22790743 | 8.062144315 | 8.305752994 |
| 2.515737189 | 11.09586997 | 10.62093659 | 2.086691569 | 6.573729137 | 6.211395518 |
| 2.295664462 | 8.776303428 | 8.724370064 | 2.670197948 | 12.72388637 | 13.54589528 |
| 2.027718522 | 5.952153222 | 6.256775374 | 2.000091181 | 5.66096105 | 5.646931808 |
| 2.763988793 | 13.71244188 | 13.89392379 | 1.960280046 | 5.241351681 | 4.939545369 |
| 2.076496541 | 6.466273545 | 6.726483336 | 2.397598317 | 9.850686263 | 9.836570257 |
| 2.303703647 | 8.861036436 | 9.564694728 | 2.973791694 | 15.92376445 | 16.77320637 |
| 2.026693302 | 5.941347407 | 5.857504246 | 2.231093337 | 8.09572377 | 8.154869208 |
| 2.316152864 | 8.992251184 | 9.130349864 | 2.327582721 | 9.112721878 | 8.620686086 |
| 2.5491395 | 11.44793033 | 11.16907736 | 2.172851247 | 7.481852144 | 7.195997594 |
| 2.083746633 | 6.542689513 | 5.669034365 | 2.601108292 | 11.99568139 | 11.3585644 |
| 2.943704329 | 15.60664363 | 15.01258793 | 2.157362461 | 7.318600337 | 7.622097141 |
| 2.69404096 | 12.97519171 | 11.50064588 | 2.483366853 | 10.75468663 | 11.34479687 |
| 2.069147144 | 6.388810897 | 6.627639543 | 2.274443402 | 8.552633458 | 8.864232826 |
| 1.915810452 | 4.77264216 | 4.981779331 | 2.592234096 | 11.90214737 | 11.42566893 |
| 2.155425119 | 7.298180756 | 7.306583156 | 2.465123015 | 10.56239658 | 11.35661385 |
| 2.365948982 | 9.517102268 | 9.022670875 | 2.330163415 | 9.139922397 | 9.538773713 |
| 2.092370411 | 6.633584136 | 6.947099234 | 2.221842452 | 7.998219447 | 7.483712031 |
| 2.358711834 | 9.440822728 | 9.465047225 | 1.895096493 | 4.554317036 | 4.413260102 |
| 2.251115743 | 8.306759929 | 8.352283261 | 2.167301475 | 7.423357548 | 7.325356837 |
| 2.369996349 | 9.559761519 | 9.257760832 | 1.982391058 | 5.47440175 | 5.683424284 |
| 2.613721947 | 12.12862932 | 12.08109166 | 2.612521044 | 12.11597181 | 12.48160496 |
| 2.154976047 | 7.293447531 | 7.405363699 | 1.996568009 | 5.623826814 | 5.036731528 |
| 2.108068601 | 6.799043053 | 6.808558632 | 2.269412727 | 8.499610145 | 8.560400307 |
| 2.264025662 | 8.442830474 | 8.577407748 | 2.102320693 | 6.738460107 | 6.878566663 |
| 1.867080394 | 4.259027352 | 3.405893273 | 2.230827182 | 8.092918497 | 7.873933132 |
| 2.465979587 | 10.57142485 | 10.91048486 | 1.950857541 | 5.142038481 | 4.546899756 |
| 1.988629906 | 5.540159205 | 5.621465267 | 2.156493579 | 7.309442318 | 7.152618071 |
| 1.737499556 | 2.893245317 | 3.186618543 | 2.298608536 | 8.807333967 | 8.476315302 |
| 1.878376228 | 4.378085447 | 4.535839646 | 2.46482197 | 10.55922356 | 10.92321281 |
| 1.976222868 | 5.409389029 | 5.330493323 | 2.46398694 | 10.55042234 | 10.21092586 |
| 2.028765408 | 5.963178403 | 6.03106399 | 2.318576092 | 9.017792013 | 8.882762347 |
| 2.124386041 | 6.971028872 | 7.14402088 | 2.229769846 | 8.081774176 | 8.128596709 |
| 2.040453291 | 6.086377683 | 6.177487284 | 2.607937205 | 12.06765814 | 12.10452682 |
| 2.142885648 | 7.16601473 | 7.189024095 | 1.877462048 | 4.36844999 | 4.966870029 |

TABLE 4

| Non-maternal allele fraction | Estimated fetal fraction (1000GP3) | Baseline fetal fraction | Non-maternal allele fraction | Estimated fetal fraction (1000GP3) | Baseline fetal fraction |
| --- | --- | --- | --- | --- | --- |
| 3.951365645 | 5.400817483 | 5.761554111 | 3.652358143 | 3.678235262 | 3.636890661 |
| 4.85908685 | 10.63019934 | 10.11203623 | 4.32868846 | 7.574574219 | 7.742588045 |
| 5.307355688 | 13.21267612 | 12.85038896 | 4.453357696 | 8.292793687 | 8.395942656 |
| 4.770804746 | 10.12160614 | 9.959589059 | 3.931839385 | 5.288326699 | 5.47941978 |
| 4.963133566 | 11.22961247 | 12.16462095 | 4.673172938 | 9.559149294 | 10.18235405 |
| 4.72825721 | 9.876489787 | 10.09884697 | 4.649516644 | 9.422865389 | 9.01684116 |
| 3.789810382 | 4.470097609 | 3.945468953 | 4.871919511 | 10.7041283 | 11.13212246 |
| 4.896183189 | 10.84391135 | 10.54402542 | 4.355430792 | 7.728636796 | 8.305752994 |
| 4.94750508 | 11.13957677 | 10.62093659 | 4.093939017 | 6.222182674 | 6.211395518 |
| 4.497413114 | 8.546596952 | 8.724370064 | 5.271760437 | 13.00761188 | 13.54589528 |
| 4.00454596 | 5.707189277 | 6.256775374 | 4.0182621 | 5.786207958 | 5.646931808 |
| 5.35892892 | 13.50978951 | 13.89392379 | 3.999566525 | 5.678502748 | 4.939545369 |
| 4.182350174 | 6.731519355 | 6.726483336 | 4.686463844 | 9.635718203 | 9.836570257 |
| 4.486093336 | 8.481383709 | 9.564694728 | 5.774880023 | 15.90608381 | 16.77320637 |
| 3.99998742 | 5.680927525 | 5.857504246 | 4.443079021 | 8.233578242 | 8.154869208 |
| 4.480317959 | 8.44811176 | 9.130349864 | 4.589619939 | 9.077800468 | 8.620686086 |
| 5.051209506 | 11.73701797 | 11.16907736 | 4.361246154 | 7.762139093 | 7.195997594 |
| 4.103249721 | 6.275821641 | 5.669034365 | 5.086214665 | 11.93868269 | 11.3585644 |
| 5.740941632 | 15.71056474 | 15.01258793 | 4.24707194 | 7.104381444 | 7.622097141 |
| 5.197977606 | 12.58254899 | 11.50064588 | 4.791190104 | 10.23904619 | 11.34479687 |
| 4.046095608 | 5.946556799 | 6.627639543 | 4.513705191 | 8.640455608 | 8.864232826 |
| 3.804484305 | 4.554634081 | 4.981779331 | 5.172863205 | 12.43786493 | 11.42566893 |
| 4.379792439 | 7.86898424 | 7.306583156 | 4.891887933 | 10.81916638 | 11.35661385 |
| 4.643999061 | 9.391078588 | 9.022670875 | 4.632975536 | 9.327572061 | 9.538773713 |
| 4.175756487 | 6.693533121 | 6.947099234 | 4.413412514 | 8.062669496 | 7.483712031 |
| 4.692525719 | 9.670640666 | 9.465047225 | 3.891732558 | 5.057271266 | 4.413260102 |
| 4.440413776 | 8.218223761 | 8.352283261 | 4.364503927 | 7.780907122 | 7.325356837 |
| 4.682851601 | 9.614908074 | 9.257760832 | 3.898089172 | 5.09389172 | 5.683424284 |
| 5.09762677 | 12.00442782 | 12.08109166 | 5.040884898 | 11.6775379 | 12.48160496 |
| 4.294650086 | 7.378479147 | 7.405363699 | 3.97252184 | 5.522698322 | 5.036731528 |
| 4.179678289 | 6.716126624 | 6.808558632 | 4.445132708 | 8.245409529 | 8.560400307 |
| 4.444524422 | 8.241905195 | 8.577407748 | 4.132938535 | 6.446858903 | 6.878566663 |
| 3.71192918 | 4.021424003 | 3.405893273 | 4.47024133 | 8.390060302 | 7.873933132 |
| 4.848438758 | 10.56885569 | 10.91048486 | 3.872221407 | 4.944867528 | 4.546899756 |
| 4.02356046 | 5.816731812 | 5.621465267 | 4.294980799 | 7.380384384 | 7.152618071 |
| 3.513727216 | 2.879582489 | 3.186618543 | 4.595709778 | 9.112884032 | 8.476315302 |
| 3.737540335 | 4.168969872 | 4.535839646 | 4.794241682 | 10.25662633 | 10.92321281 |
| 3.949244868 | 5.388599683 | 5.330493323 | 4.811250199 | 10.3546124 | 10.21092586 |
| 4.179548881 | 6.715381105 | 6.03106399 | 4.602280665 | 9.150738913 | 8.882762347 |
| 4.182577499 | 6.732828974 | 7.14402088 | 4.457575783 | 8.317094086 | 8.128596709 |
| 4.165197986 | 6.632705598 | 6.177487284 | 5.092368865 | 11.97413703 | 12.10452682 |
| 4.258721943 | 7.171497115 | 7.189024095 | 3.82126678 | 4.651317922 | 4.966870029 |

4. Coverage Test

In order to confirm whether the accuracy of fetal fraction measurement was maintained or not regardless of reducing a sequencing coverage, the number of reads was randomly determined between 100K and 3,000K.

The number of reads, the numbers of SNVs subjected to MAF filtering at 0.5% (HRC v1.1) and 7.0% (1000GP3), correlation coefficients based on baseline, correlation coefficients based on the Y chromosome-based results, and coverages were obtained, and the results are shown in Table 5.

TABLE 5

| | Before imputation | | | | |
| --- | --- | --- | --- | --- | --- |
| Number of reads | 100,000 | 200,000 | 400,000 | 500,000 | 700,000 |
| Number of SNVs | 5,039 | 10,043 | 19,976 | 24,886 | 34,616 |
| Correlation coefficient (based on baseline) | 0.62760 | 0.85073 | 0.89303 | 0.92558 | 0.92547 |

TABLE 5-continued

| | | | | | |
|---|---|---|---|---|---|
| Correlation coefficient (based on Y chromosome-based results) | 0.61865 | 0.71756 | 0.78376 | 0.81468 | 0.84549 |
| coverage | 0.005 | 0.01 | 0.02 | 0.025 | 0.03 |
| SNP imputation with HRC v1.1 (MAF ≥0.5%) | | | | | |
| Number of reads | 100,000 | 200,000 | 400,000 | 500,000 | 700,000 |
| Number of SNVs | 44,143 | 87,924 | 174,639 | 217,651 | 302,822 |
| Correlation coefficient (with baseline results) | 0.92011 | 0.9664 | 0.97981 | 0.98245 | 0.98310 |
| Correlation coefficient (with Y chromosome-based results) | 0.88038 | 0.91633 | 0.92646 | 0.93369 | 0.93199 |
| Coverage | 0.005 | 0.01 | 0.02 | 0.025 | 0.03 |
| SNP imputation with 1000GP3 (MAF ≥7%) | | | | | |
| Number of reads | 100,000 | 200,000 | 400,000 | 500,000 | 700,000 |
| Number of SNVs | 29,584 | 58,679 | 116,115 | 144,504 | 200,771 |
| Correlation coefficient (based on baseline) | 0.85438 | 0.95036 | 0.95854 | 0.96407 | 0.97005 |
| Correlation coefficient (based on Y chromosome-based results) | 0.79546 | 0.89586 | 0.91689 | 0.91528 | 0.91174 |
| coverage | 0.005 | 0.01 | 0.02 | 0.025 | 0.03 |

| | Before imputation | | | |
|---|---|---|---|---|
| Number of reads | 1,000,000 | 2,000,000 | 3,000,000 | 5,351,786 |
| Number of SNVs | 48,960 | 94,877 | 137,947 | 247,596 |
| Correlation coefficient (based on baseline) | 0.96256 | 0.98389 | 0.98752 | 1 |
| Correlation coefficient (based on Y chromosome-based results) | 0.90056 | 0.91223 | 0.91251 | 0.92827 |
| coverage | 0.05 | 0.1 | 0.15 | 0.3 |
| SNP imputation with HRC v1.1 (MAF ≥0.5%) | | | | |
| Number of reads | 1,000,000 | 2,000,000 | 3,000,000 | 5,351,786 |
| Number of SNVs | 428,451 | 830,769 | 1,209,161 | 2,178,642 |
| Correlation coefficient (with baseline results) | 0.98157 | 0.98854 | 0.98743 | 0.98910 |
| Correlation coefficient (with Y chromosome-based results) | 0.93668 | 0.94362 | 0.94272 | 0.94041 |
| Coverage | 0.05 | 0.1 | 0.15 | 0.3 |
| SNP imputation with 1000GP3 (MAF ≥7%) | | | | |
| Number of reads | 1,000,000 | 2,000,000 | 3,000,000 | 5,351,786 |
| Number of SNVs | 283,541 | 548,683 | 797,911 | 1,438,097 |
| Correlation coefficient (based on baseline) | 0.97498 | 0.98058 | 0.98125 | 0.98417 |

TABLE 5-continued

| Correlation coefficient (based on Y chromosome-based results) | 0.93162 | 0.93343 | 0.93351 | 0.93804 |
|---|---|---|---|---|
| coverage | 0.05 | 0.1 | 0.15 | 0.3 |

Figure 3:
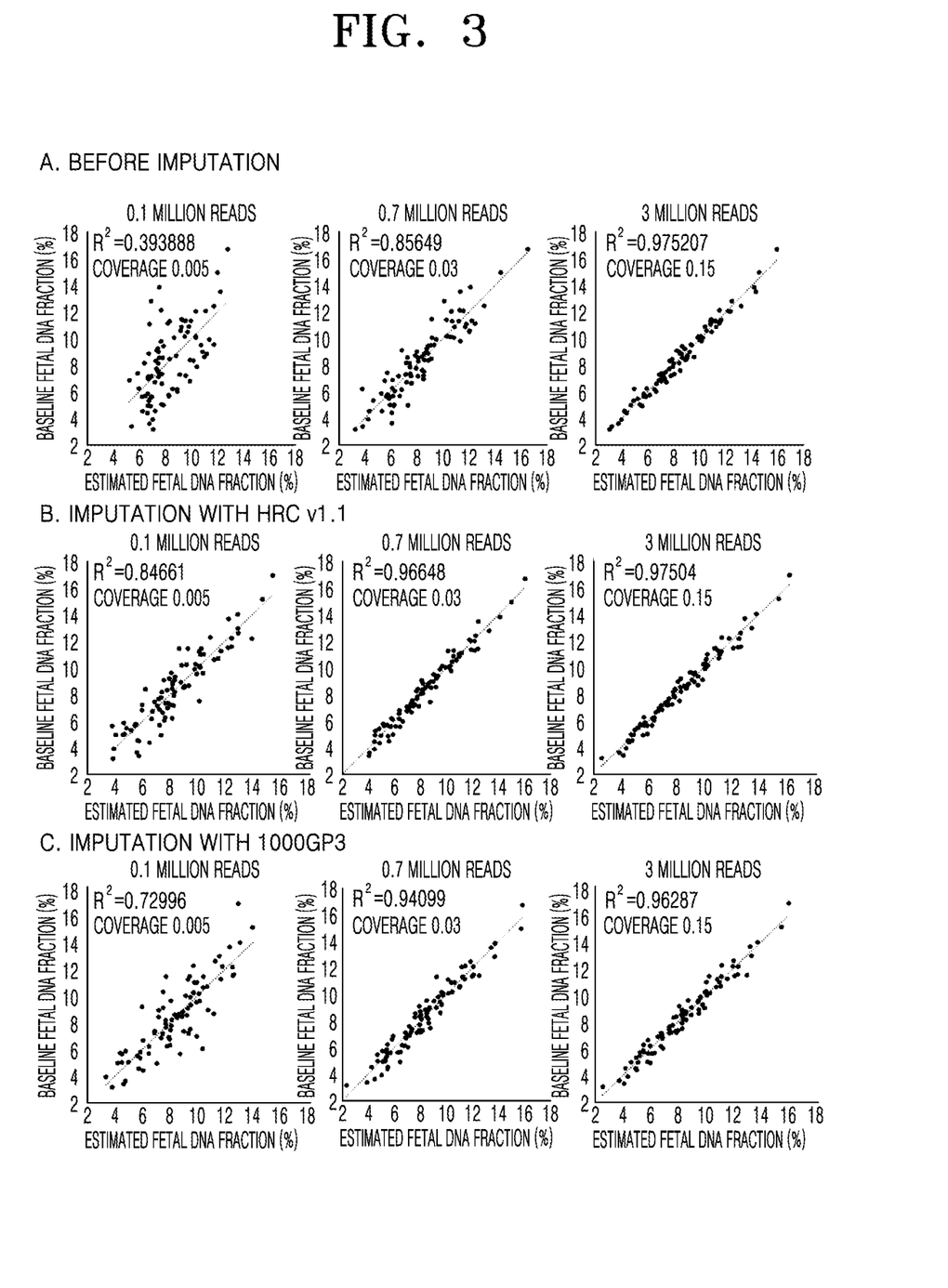
FIG. 3 is a graph showing a correlation between an estimated fetal DNA fraction and a baseline fetal DNA fraction (A: when an imputation is not performed, B: when SNP imputation is performed with HRC v1.1 as a reference panel, and C: when SNP imputation is performed with 1000GP3 as a reference panel)

As shown in Table 5, correlation coefficients were generally low when the sequencing coverage was ≤0.03 before SNP imputation. At 0.005× sequencing coverage, the correlation coefficient ($R^2$=0.39) dramatically decreased. In contrast, when SNP imputation was performed using the HRC v1.1 reference panel, the correlation coefficient ($R^2$=0.85) was high even after the sequencing coverage was reduced to 0.005. Similarly, a strong correlation ($R^2$=0.73) was observed when imputation was performed using 1000GP3 relative to when no imputation was performed. FIG. 3 is a graph showing the correlation between the measured fetal DNA fractions and baseline fetal DNA fractions (A: when an imputation is not performed, B: when SNP imputation is performed with HRC v1.1 as a reference panel, and C: when SNP imputation is performed with 1000GP3 as a reference panel).

Figure 4:
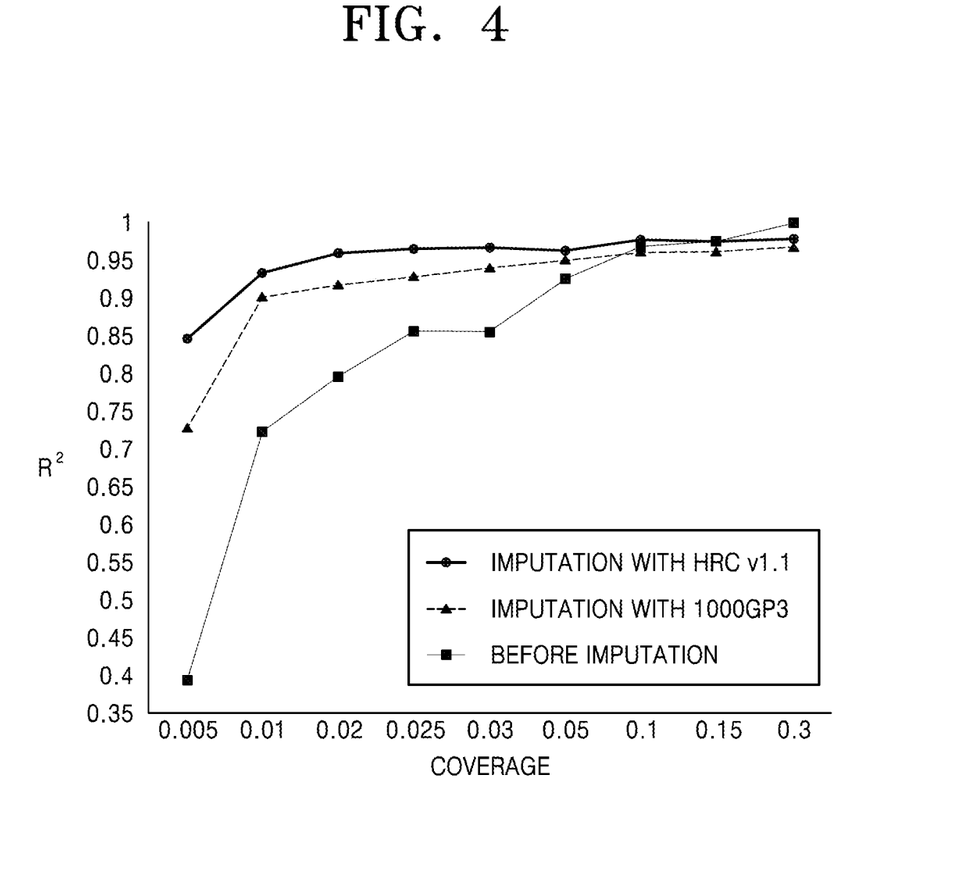
FIG. 4 is a graph of correlation coefficients ($R^2$) in terms of performing and not performing an imputation.

Also, FIG. 4 is a graph showing the correlation coefficient ($R^2$) with respect to the sequencing coverage according to performing or not performing imputation.

As shown in FIGS. 3 and 4, when no imputation was performed, the correlation was much weaker as coverage was lowered to <0.03. However, when imputation was performed, the correlation coefficient remained high even after coverage was reduced to 0.01 (0.2 million reads). Therefore, it was confirmed that when a fetal fraction is estimated by performing a SNP imputation, the accuracy of fetal fraction imputation maintained even when a sequencing coverage is reduced.

The invention claimed is:

1. A method of determining a fetal fraction, the method comprising:
    obtaining sequence information (reads) of a plurality of nucleic acid fragments from a biological sample of a pregnant woman;
    genotyping single nucleotide polymorphisms (SNPs) from the biological sample;
    measuring single nucleotide variants (SNVs) by performing an SNP imputation on the genotyped SNPs;
    measuring a non-maternal allele fraction based on the obtained reads and the SNVs;
    filtering a minor allele frequency (MAF) after the measuring of the SNVs, wherein the filtering of the MAF is performed on at least one chromosome;
    determining a fetal fraction from the non-maternal allele fraction; and
    performing an invasive diagnostic method selected from chorionic villus sampling, amniocentesis, and umbilical cordocentesis, based on the determining a fetal fraction from the non-maternal allele fraction.

2. The method of claim 1, wherein the biological sample is blood, plasma, serum, urine, saliva, mucus, sputum, feces, tears, or a combination thereof.

3. The method of claim 1, wherein the biological sample is fetal nucleic acids.

4. The method of claim 1, wherein the obtaining of the reads comprises isolating cell-free DNAs (cfDNAs) from the biological sample.

5. The method of claim 1, wherein a sequencing coverage of the obtained reads is in a range of about 0.00001 to about 1.

6. The method of claim 1, wherein a number of the SNPs genotyped from the obtained biological sample is in a range of 10 to 10,000,000.

7. The method of claim 1, wherein the SNP imputation comprises determining of missing SNP by comparing the genotyped SNPs with a reference panel.

8. The method of claim 7, wherein the reference panel is selected from the group consisting of HapMap, Haplotype Reference Consortium (HRC) vi.1,1000Genome phase 1 (1000GP1), 1000Genome phase 3 (1000GP3), and Consortium on Asthma among African-ancestry Populations in the Americas (CAAPA).

9. The method of claim 1, wherein the SNP imputation is performed using a software selected from the group consisting of MaCH, Minimac, IMPUTE2, Beagle, and SHAPEIT2.

10. The method of claim 1, wherein the filtering of the MAF is performed on chromosome 3 or chromosome 4.

11. The method of claim 1, wherein the filtering of the MAF comprises excluding SNVs having an MAF value less than about 0.5% with respect to chromosome 4, excluding SNVs having an MAF value less than about 7% with respect to chromosome 3, or a combination thereof.

12. The method of claim 1, wherein the determining of the fetal fraction comprises determining the fetal fraction according to the following Equation 1 or Equation 2:

$$F=10.54X-15.42 \qquad \text{(Equation 1); and}$$

$$F=5.76X-17.36 \qquad \text{(Equation 2),}$$

wherein, in Equation 1 and Equation 2, F is a fetal fraction (%), and X is a non-maternal allele fraction (%).

* * * * *